United States Patent [19]

Otaka et al.

[11] Patent Number: 5,004,753

[45] Date of Patent: Apr. 2, 1991

[54] CARBOXYLIC ACID ESTERS, METHOD FOR THEIR PRODUCTION AND INSECTICIDES CONTAINING THEM AS ACTIVE INGREDIENT

[75] Inventors: Ken Otaka, Takarazuka; Noritada Matsuo, Itami; Kazunori Tsushima, Nishinomiya; Toshihiko Yano, Ashiya, all of Japan

[73] Assignee: Sumitomo Chemical Company, Limited, Osaka, Japan

[21] Appl. No.: 512,506

[22] Filed: Apr. 20, 1990

Related U.S. Application Data

[63] Continuation of Ser. No. 186,933, Apr. 27, 1988, abandoned.

[30] Foreign Application Priority Data

May 12, 1987 [JP] Japan ................. 62-116219

[51] Int. Cl.$^5$ .............................................. A01N 53/00
[52] U.S. Cl. ..................................... 514/531; 560/124
[58] Field of Search ...................... 560/124; 514/531

[56] References Cited

U.S. PATENT DOCUMENTS 4,118,505 10/1978 Kitamura et al. .................... 514/531
4,707,498 11/1987 Kolb et al. ........................... 564/509

FOREIGN PATENT DOCUMENTS 0114012 7/1984 European Pat. Off. .
0202500 11/1986 European Pat. Off. .
2093830 9/1982 United Kingdom ................. 560/124
2174700 11/1986 United Kingdom .

*Primary Examiner*—Michael L. Shippen
*Attorney, Agent, or Firm*—Stevens, Davis, Miller & Mosher

[57] ABSTRACT

This invention relates to novel carboxylic acid esters represented by the formula (I) below, methods for their production and insecticides containing them as an active ingredient, and an alcohol compound useful as an intermediate for manufacturing carboxylic acid esters represented by the formula (I),

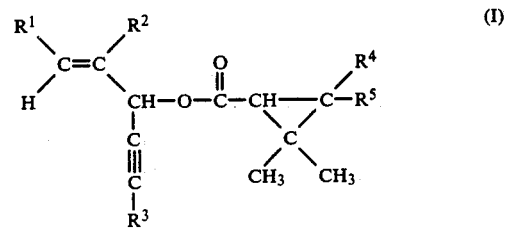

wherein $R^1$ represents a halogenated lower alkyl group, $R^2$ represents a fluorine atom or a methyl group, $R^3$ represents a hydrogen atom or a methyl group, $R^4$ represents a hydrogen atom or a methyl group, and when $R^4$ is a hydrogen atom, $R^5$ represents a group of the formula,

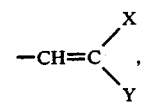

in which X and Y are the same or different and represent a hydrogen atom, a methyl group, a halogen atom or a halogenated lower alkyl group, and when $R^4$ is a methyl group, $R^5$ represents a methyl group.

6 Claims, No Drawings

CARBOXYLIC ACID ESTERS, METHOD FOR THEIR PRODUCTION AND INSECTICIDES CONTAINING THEM AS ACTIVE INGREDIENT

This application is a Continuation of application Ser. No. 07/186,933, filed Apr. 27, 1988.

The present invention relates to a novel carboxylic acid ester, a method for its production and insecticides containing it as an active ingredient.

Hitherto, the ester compound described for example in Japanese published examined patent application No. 42045/1980 or British patent application No. 2174700-A is known to have an insecticidal activity However, the insecticidal effect of the compound is not always said to be satisfactory.

In view of the situation like this, the present inventors extensively studied to develop a compound having excellent insecticidal activity, and as a result, found that an ester compound represented by the formula (I) (hereinafter referred to as present compound) has a very high insecticidal activity:

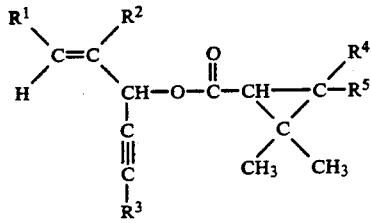

wherein $R^1$ represents a lower haloalkyl group (e.g. fluorinated, chlorinated or brominated $C_1$-$C_4$ alkyl group), $R^2$ represents a fluorine atom or a methyl group, $R^3$ represents a hydrogen atom or a methyl group, $R^4$ represents a hydrogen atom or a methyl group, and when $R^4$ represents a hydrogen atom, $R^5$ represents a group of the formula,

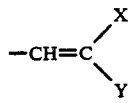

[in which X and Y may be the same or different and represent a hydrogen atom, methyl group, halogen atom (e.g. fluorine, chlorine, bromine) or lower haloalkyl group (e.g. fluorinated, chlorinated or brominated $C_1$-$C_3$ alkyl group)] and when $R_4$ represents a methyl group, $R_5$ represents a methyl group. The present inventors thus attained to the present invention.

The present compounds have excellent properties such as:

1. Acts on various insect pests very rapidly and also with a high insecticidal activity.
2. Has a high activity as a volatile formulation or smoking formulation.
3. Has a high knock-down effect especially by application of oil spray.

For insect pests against which the present compounds are particularly efficacious, there are given insect pests of Diptera such as housefly (*Musca domestica*), common mosquito (*Culex pipiens pallens*), etc., household insect pests of Lepidoptera such as case-making clothes moth (*Tinea pellionella*), webbing clothes moth (*Tineola bisselliella*), etc., insect pests of Dictyoptera such as German cockroach (*Blattella germanica*), etc. The present compounds have particularly a high activity against these insect pests in the form of volatile formulation, smoking formulation or oil formulation. Other insect pests against which the present compounds are efficacious include Hemiptera such as planthoppers, leafhoppers, aphides, bugs, etc., Lepidoptera such as diamond-back moth (*Plutella xylostella*), rice stem borer (*Chilo suppressalis*), armyworms and cutworms, etc., Coleoptera such as dermestid beetles, etc., Orthoptera, and the like.

Among the present compounds, preferred ones are those in which $R^1$ is a halogenated $C_1$-$C_4$, preferably $C_1$-$C_3$, alkyl group, $R^2$ is a fluorine atom or a methyl group, $R^3$ is a hydrogen atom, $R^4$ is a hydrogen atom or a methyl group, and when $R^4$ is a hydrogen atom, $R^5$ is a group of the formula,

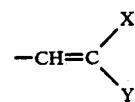

(in which X and Y may be the same or different and represent a methyl group, a fluorine, chlorine or bromine atom or a trifluoromethyl group) and when $R^4$ is a methyl group, $R^5$ is a methyl group. Of these compounds, those in which $R^1$ is a 2-fluoroethyl or 2-chloroethyl group are more preferred.

For the present compounds, there may be given for example the following compounds:

4,7-Difluoro-4-hepten-1-yne-3-yl 2,2-dimethyl-3-(2,2-dichlorovinyl)cyclopropane-1-carboxylate 7-Chloro-4-fluoro-4-hepten-1-yne-3-yl 2,2-dimethyl-3-(2,2-dichlorovinyl)cyclopropane-1-carboxylate 4,6,6,6-Tetrafluoro-4-hexen-1-yne-3-yl 2,2-dimethyl-3-(2-methyl-1-propenyl)cyclopropane-1-carboxylate 6,6,6-Trifluoro-4-methyl-4-hexen-1-yne-3-yl 2,2-dimethyl-3-(2,2-difluorovinyl)cyclopropane-1-carboxylate 4,7-Difluoro-4-hepten-1-yne-3-yl 2,2-dimethyl-3-(2,2-dibromovinyl)cyclopropane-1-carboxylate 4,7,7,7-Tetrafluoro-4-hepten-1-yne-3-yl 2,2-dimethyl-3-(2-methyl-1-propenyl)cyclopropane-1-carboxylate 4,6-Difluoro-4-hexen-1-yne-3-yl 2,2-dimethyl-3-(2-chloro-3,3,3-trifluoro-1-propenyl)cyclopropane-1-carboxylate 6,6,7,7,7-Pentafluoro-4-methyl-4-hepten-1-yne-3-yl 2,2-dimethyl-3-(2,2-dichlorovinyl)cyclopropane-1-carboxylate 7-Chloro-4-fluoro-4-hepten-1-yne-3-yl 2,2-dimethyl-3-(2-methyl-1-propenyl)cyclopropane-1-carboxylate 4,7-Difluoro-4-hepten-1-yne-3-yl 2,2-dimethyl-3-(2-chloro-3,3,3-trifluoro-1-propenyl)cyclopropane-1-carboxylate 4,6,6,6-Tetrafluoro-4-hexen-1-yne-3-yl 2,2-dimethyl-3-(2,2-dichlorovinyl)cyclopropane-1-carboxylate 6,6,6-Trifluoro-4-methyl-4-hexen-1-yne-3-yl 2,2-dimethyl-3-(2-methyl-1-propenyl)cyclopropane-1-carboxylate 6,6,7,7,7-Pentafluoro-4-methyl-4-hepten-1-yne-3-yl 2,2-dimethyl-3-(2-methyl-1-propenyl)cyclopropane-1-carboxylate 7-Fluoro-4-methyl-4-hepten-1-yne-3-yl 2,2-dimethyl-3-(2,2-dichlorovinyl)cyclopropane-1-carboxylate 4,7-Difluoro-4-hepten-1-yne-3-yl 2,2-dimethyl-3-(2-methyl-1-propenyl)cyclopropane-1-carboxylate 4,6-Difluoro-4-hepten-1-yne-3-yl 2,2-dimethyl-3-(2,2-dichlorovinyl)cylcopropane-1-carboxylate 6,6,7,7,8,8,8-Heptafluoro-4-methyl-4-octen-1-yne-3-yl 2,2-dimethyl-3-(2,2-dichlorovinyl)cyclopropane-1-carboxylate 7-Chloro-4-fluoro-4-hepten-1-yne-3-yl 2,2-dimethyl-3-(2,2-dibromovinyl)cyclopropane-1-carboxylate 6,6,6-Trifluoro-4-methyl-4-hexen-1-yne-3-yl 2,2-dimethyl-3-(2,2-dichlorovinyl)cyclopropane-1-carboxylate 6,6,7,7,7-Pentafluoro-4-methyl-4-hepten-1-yne-3-yl 2,2-dimethyl-3-(2,2-difluorovinyl)cyclopropane-1-carboxylate 4,6-Difluoro-4-hexen-1-yne-3-yl 2,2-dimethyl-3-(2,2-dichlorovinyl)cyclopropane-1-carboxylate 4,7,7-Trifluoro-4-hepten-1-yne-3-yl 2,2-dimethyl-3-(2-methyl-1-propenyl)cyclopropane-1-carboxylate 4,7,7,7-Tetrafluoro-4-hepten-1-yne-3-yl 2,2-dimethyl-3-(2,2-dichlorovinyl)cyclopropane-1-carboxylate 7-Chloro-4-fluoro-4-hepten-1-yne-3-yl 2,2-dimethyl-3-(2-chloro-3,3,3-trifluoro-1-propenyl)cyclopropane-1-carboxylate 6,6,6-Trifluoro-4-methyl-4-hexen-1-yne-3-yl 2,2-dimethyl-3-(2,2-dibromovinyl)cyclopropane-1-carboxylate 4,8-Difluoro-4-octen-1-yne-3-yl 2,2-dimethyl-3-(2,2-dichlorovinyl)cyclopropane-1-carboxylate 4,6,6,6-Tetrafluoro-4-hexen-1-yne-3-yl 2,2-dimethyl-3-(2,2-difluorovinyl)cyclopropane-1-carboxylate 4,7-Difluoro-4-hepten-1-yne-3-yl 2,2-dimethyl-3-(2,2-difluorovinyl)cyclopropane-1-carboxylate 7-Chloro-4-fluoro-4-hepten-1-yne-3-yl 2,2-dimethyl-3-(2,2-difluorovinyl)cyclopropane-1-carboxylate 6,6,6-Trifluoro-4-methyl-4-hexen-1-yne-3-yl 2,2-dimethyl-3-(2-chloro-3,3,3-trifluoro-1-propenyl)cyclopropane-1-carboxylate 6,6,7,7,7-Pentafluoro-4-methyl-4-hepten-1-yne-3-yl 2,2-dimethyl-3-(2,2-dibromovinyl)cyclopropane-1-carboxylate 4,6,6,6-Tetrafluoro-4-hexen-1-yne-3-yl 2,2-dimethyl-3-(2,2-dibromovinyl)cyclopropane-1-carboxylate 4,6,6,7,7,7-Hexafluoro-4-hepten-1-yne-3-yl 2,2-dimethyl-3-(2,2-dibromovinyl)cyclopropane-1-carboxylate 4,7,7-Trifluoro-4-hepten-1-yne-3-yl 2,2-dimethyl-3-(2,2-dichlorovinyl)cyclopropane-1-carboxylate 7,7-Difluoro-4-methyl-4-hepten-1-yne-3-yl 2,2-dimethyl-3-(2,2-dichlorovinyl)cyclopropane-1-carboxylate 4,8-Difluoro-4-octen-1-yne-3-yl 2,2-dimethyl-3-(2-methyl-1-propenyl)cyclopropane-1-carboxylate 6-Chloro-4-fluoro-4-hexen-1-yne-3-yl 2,2-dimethyl-3-(2,2-dichlorovinyl)cyclopropane-1-carboxylate 7-Fluoro-4-methyl-4-hepten-1-yne-3-yl 2,2-dimethyl-3-(2-methyl-1-propenyl)cyclopropane-1-carboxylate 7,7,7-Trifluoro-4-methyl-4-hepten-1-yne-3-yl 2,2-dimethyl-3-(2,2-dichlorovinyl)cyclopropane-1-carboxylate 7,7-Difluoro-4-methyl-4-hepten-1-yne-3-yl 2,2-dimethyl-3-(2-methyl-1-propenyl)cyclopropane-1-carboxylate 7-Fluoro-4-methyl-4-hepten-1-yne-3-yl 2,2-dimethyl-3-(2-chloro-3,3,3-trifluoro-1-propenyl)cyclopropane-1-carboxylate 4,6-Difluoro-4-hexen-1-yne-3-yl 2,2-dimethyl-3-(2,2-dibromovinyl)cyclopropane-1-carboxylate 4,7,7,7-Tetrafluoro-4-hepten-1-yne-3-yl 2,2-dimethyl-3-(2,2-difluorovinyl)cyclopropane-1-carboxylate 6,6,7,7,7-Pentafluoro-4-methyl-4-hepten-1-yne-3-yl 2,2-dimethyl-3-(2-chloro-3,3,3-trifluoro-1-propenyl)cyclopropane-1-carboxylate 4,6,6,6-Tetrafluoro-4-hexen-1-yne-3-yl 2,2-dimethyl-3-(2-chloro-3,3,3-trifluoro-1-propenyl)cyclopropane-1-carboxylate 7-Chloro-4-methyl-4-hepten-1-yne-3-yl 2,2-dimethyl-3-(2-methyl-1-propenyl)cyclopropane-1-carboxylate 4,6,6,7,7-Hexafluoro-4-hepten-1-yne-3-yl 2,2-dimethyl-3-(2,2-dichlorovinyl)cyclopropane-1-carboxylate 7,7,7-Trifluoro-4-methyl-4-hepten-1-yne-3-yl 2,2-dimethyl-3-(2-methyl-1-propenyl)cyclopropane-1-carboxylate 4,6-Difluoro-4-hepten-1-yne-3-yl 2,2-dimethyl-3-(2,2-dibromovinyl)cyclopropane-1-carboxylate 7-Chloro-4-methyl-4-hepten-1-yne-3-yl 2,2-dimethyl-3-(2,2-dichlorovinyl)cyclopropane-1-carboxylate 6-Chloro-4-fluoro-4-hexen-1-yne-3-yl 2,2-dimethyl-3-(2-methyl-1-propenyl)cyclopropane-1-carboxylate 5,8-Difluoro-5-octen-2-yne-4-yl 2,2-dimethyl-3-(2,2-dichlorovinyl)cyclopropane-1-carboxylate 7,7,7-Trifluoro-5-methyl-5-hepten-2-yne-4-yl 2,2-dimethyl-3-(2-methyl-1-propenyl)cyclopropane-1-carboxylate 4,7-Difluoro-4-hepten-1-yne-3-yl 2,2,3,3-tetramethylcyclopropane-1-carboxylate 7-Chloro-4-fluoro-4-hepten-1-yne-3-yl 2,2,3,3-tetramethylcyclopropane-1-carboxylate 5,7,7,7-Tetrafluoro-5-hepten-2-yne-4-yl 2,2-dimethyl-3-(2,2-dichlorovinyl)cyclopropane-1-carboxylate 5,7,7,7-Tetrafluoro-5-hepten-2-yne-4-yl 2,2-dimethyl-3-(2-methyl-1-propenyl)cyclopropane-1-carboxylate 6,6,6-Trifluoro-4-methyl-4-hexen-1-yne-3-yl 2,2,3,3-tetramethylcyclopropane-1-carboxylate 5,8-Difluoro-5-octen-2-yne-4-yl 2,2-dimethyl-3-(2-methyl-1-propenyl)cyclopropane-1-carboxylate 7,7,7-Trifluoro-5-methyl-5-hepten-2-yne-4-yl 2,2-dimethyl-3-(2,2-dibromovinyl)cyclopropane-1-carboxylate 5,7,7,7-Tetrafluoro-5-hepten-2-yne-4-yl 2,2-dimethyl-3-(2,2-difluorovinyl)cyclopropane-1-carboxylate 4,6,6,6-Tetrafluoro-4-hexen-1-yne-3-yl 2,2,3,3-tetramethylcyclopropane-1-carboxylate 6-Bromo-4-fluoro-4-hexen-1-yne-3-yl 2,2-dimethyl-3-(2,2-dichlorovinyl)cyclopropane-1-carboxylate 7-Bromo-4-fluoro-4-hepten-1-yne-3-yl 2,2-dimethyl-3-(2-methyl-1-propenyl)cyclopropane-1-carboxylate 7-Bromo-4-fluoro-4-hepten-1-yne-3-yl 2,2-dimethyl-3-(2,2-dichlorovinyl)cyclopropane-1-carboxylate 4,9-Difluoro-4-nonen-1-yne-3-yl 2,2-dimethyl-3-(2,2-dichlorovinyl)cyclopropane-1-carboxylate 4,7-Difluoro-4-heptan-1-yne-3-yl 2,2-dimethyl-3-(2-chloro-2-fluorovinyl)cyclopropane-1-carboxylate 4,7-Difluoro-4-hepten-1-yne-3-yl 2,2-dimethyl-3-(2-fluoro-1-propenyl)cyclopropane-1-carboxylate The present compounds include various optical isomers and geometrical isomers, and these isomers are also included in the present invention.

The present compounds can be produced by reacting an alcohol compound represented by the formula (II),

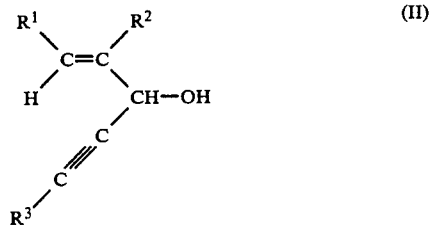

wherein $R^1$, $R^2$ and $R^3$ represent the same meanings as described above, with a carboxylic acid halide represented by the formula (III),

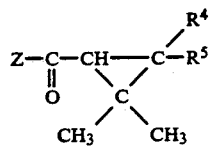

wherein Z represents a halogen atom, and $R^4$ and $R^5$ represent the same meanings as described above.

This reaction is usually carried out in an inert solvent (e.g. toluene, benzene, diethyl ether, hexane) at a temperature of from 0° to 100° for from 30 minutes to 20 hours in the presence of a base (e.g. pyridine, triethylamine). For the carboxylic acid halide represented by the formula (III), a carboxylic acid chloride is usually used.

In the foregoing method, the alcohol compound, a material, represented by the formula (II) is a novel compound, and it can be produced, for example, through the following reaction route:

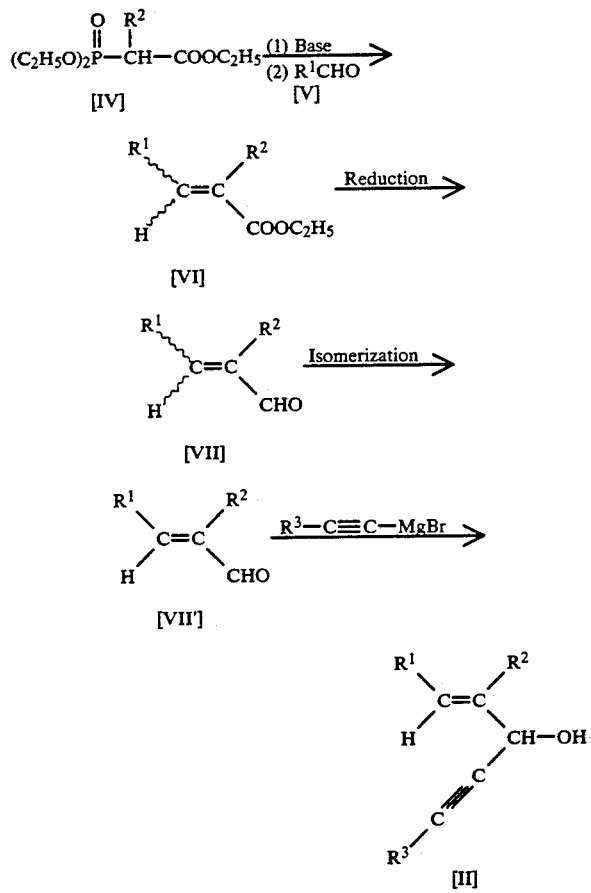

wherein $R^1$, $R^2$ and $R^3$ represent the same meanings as described above.

That is, an unsaturated ester compound represented by the formula (VI) is obtained by reacting triethyl 2-fluoro-2-phosphonoacetate or triethyl 2-phosphonopropionate represented by the formula (IV) firstly with a base (e.g. lithium diisopropylamide, sodium hydride) at a temperature of from −80° to 30° C. for from 1 to 3 hours in an inert solvent (e.g. tetrahydrofuran, dimethylformamide) and then with a haloaldehyde represented by the formula (V) (e.g. trifluoroacetaldehyde, pentafluoropropionaldehyde, 3-fluoropropionaldehyde, 3-chloropropionaldehyde, 4- fluorobutyraldehyde) at a temperature of from −70° to 30° C. for from 5 to 20 hours. This unsaturated ester compound is converted to an aldehyde compound represented by the formula (VII) by reacting it with a reducing agent (e.g. diisobutylaluminum hydride) at a temperature of from −70° to 60° C. for from 30 minutes to 2 hours in an inert solvent (e.g. toluene, hexane, diethyl ether). The aldehyde compound obtained is usually a mixture of E-form and Z-form geometrical isomers, but by treating it in an inert solvent (e.g. toluene, benzene, hexane, methylene chloride) at a temperature of from 30° to 110° C. for from 3 to 60 hours in the presence of an isomerization catalyst (e.g. sodium salt of thiophenol, iodine), it can be isomerized so as to contain a larger proportion of the geometrical isomer which is useful to produce the present compounds.

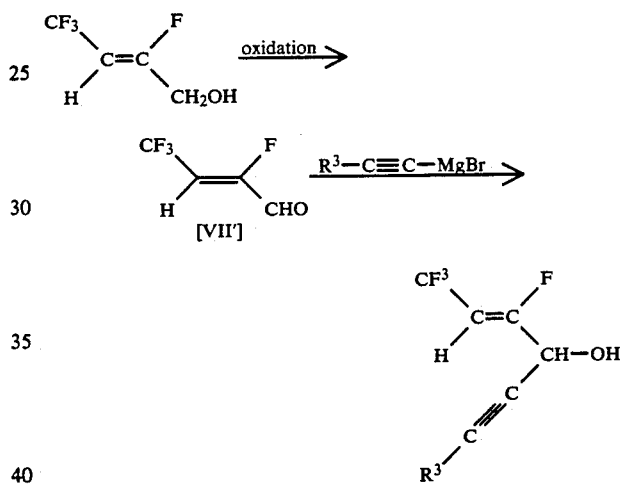

In addition, when $R^1$ is a trifluoromethyl group and $R^2$ is a fluorine atom, the aldehyde compound (VII') can also be synthesized by oxidizing the known alcohol compound with an oxidizing agent (e.g. pyridinium chlorochromate, pyridinium dichromate) at a temperature of from 0° to 40° C. in methylene chloride (See the reference: J. Fluorine Chemistry, 24, 419–430 (1984) N. Ishikawa et. al.). Next this aldehyde compound can be converted to the alcohol compound represented by the formula (II) by reacting it with ethynylmagnesium bromide or 1-propynylmagnesium bromide in an inert solvent (e.g. tetrahydrofuran) at a temperature of from 0° to 40° C. for from 5 to 20 hours.

For the alcohol compound of the formula (II) thus obtained, there are given for example the followings:
4,7-Difluoro-3-hydroxy-4-hepten-1-yne
6,6,6-Trifluoro-3-hydroxy-4-methyl-4-hexen-1-yne
6,6,7,7,7-Pentafluoro-3-hydroxy-4-methyl-4-hepten-1-yne
4,6,6,6-Tetrafluoro-3-hydroxy-4-hexen-1-yne
7,7,7-Trifluoro-3-hydroxy-4-methyl-4-hepten-1-yne
4,7,7,7-Tetrafluoro-3-hydroxy-4-hepten-1-yne
4,7,7-Trifluoro-3-hydroxy-4-hepten-1-yne
7,7-Difluoro-3-hydroxy-4-methyl-4-hepten-1-yne
4,6,6,7,7,7-Hexafluoro-3-hydroxy-4-hepten-1-yne
4,6-Difluoro-3-hydroxy-4-hepten-1-yne 6,6,7,7,8,8,8-Heptafluoro-3-hydroxy-4-methyl-4-octen-1-yne
7,7,7-Trifluoro-4-hydroxy-5-methyl-5-hepten-2-yne
5,7,7,7-Tetrafluoro-4-hydroxy-5-hepten-2-yne
4,8-Difluoro-3-hydroxy-4-octen-1-yne Further, for the aldehyde compound represented by the formula (VII'), there are given for example the followings:
2,5-Difluoro-2-pentenal
4,4,4-Trifluoro-2-methyl-2-butenal
4,4,5,5,5-Pentafluoro-2-methyl-2-pentenal
2,4,4,4-Tetrafluoro-2-butenal
5,5,5-Trifluoro-2-methyl-2-pentenal
2,5,5,5-Tetrafluoro-2-pentenal
2,5,5-Trifluoro-2-pentenal
5,5-Difluoro-2-methyl-2-pentenal
2,4,4,5,5,5-Hexafluoro-2-pentenal
2,4-Difluoro-2-pentenal
4,4,5,5,6,6,6-Heptafluoro-2-methyl-2-hexenal
2,6-Difluoro-2-hexenal Among the present compounds, particularly those which are represented by the formula (VIII),

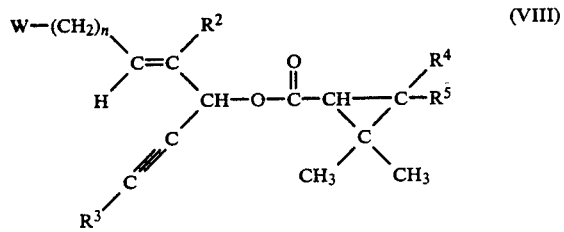

(VIII)

wherein n represents an integer of from 1 to 4, W represents a halogen atom, and $R^2$, $R^3$, $R^4$ and $R^5$ represent the same meanings as described above, can also be produced by the halogenation of a compound represented by the formula (IX),

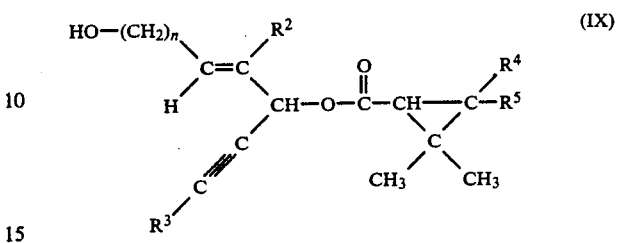

(IX)

wherein n, $R^2$, $R^3$, $R^4$ and $R^5$ represent the same meanings as described above.

This halogenation can be carried out by reacting the compound represented by the formula (IX) with a halogenating agent in an inert solvent at a temperature of from $-20°$ to $50°$ C. for from 30 minutes to 20 hours. The inert solvent includes halogenated hydrocarbons (e.g. carbon tetrachloride, chloroform, methylene chloride), hydrocarbons (e.g. toluene, hexane), ethers (e.g. diethyl ether, dimethoxyethane, tetrahydrofuran), 1-methyl-2-pyrrolidinone, etc., and the halogenating agent includes diethylaminosulfur trifluoride, thionyl chloride, thionyl bromide, triphenylphosphine/carbon tetrachloride, triphenylphosphine/carbon tetrabromide, etc.

The compound of the formula (IX), a material, used in the above halogenation is a novel compound, and it can be produced, for example, through the following reaction route:

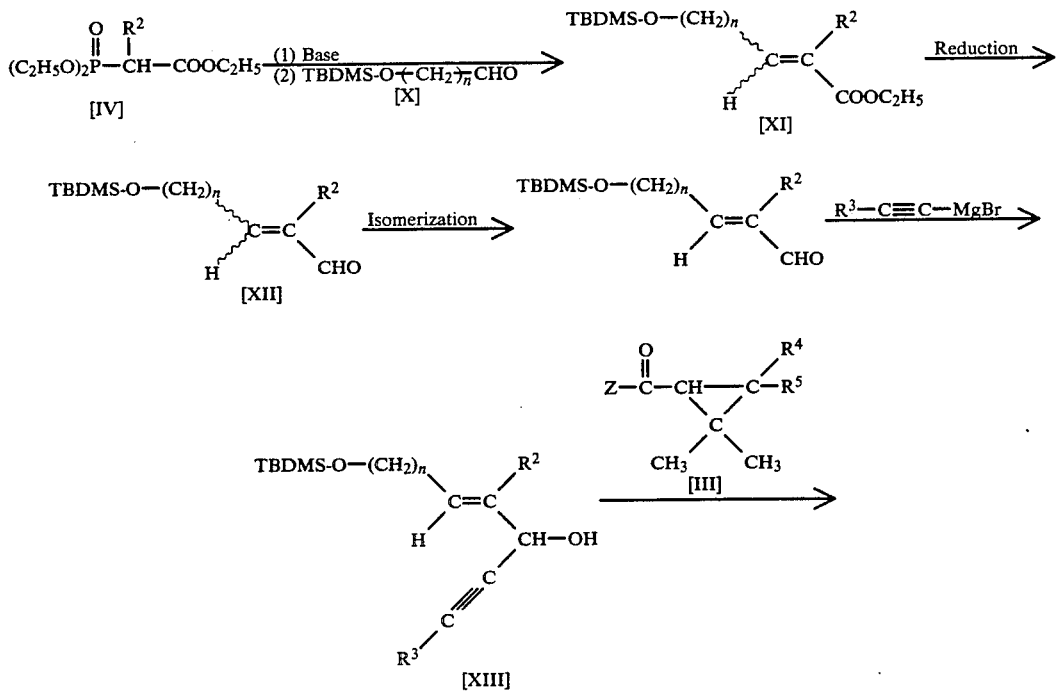

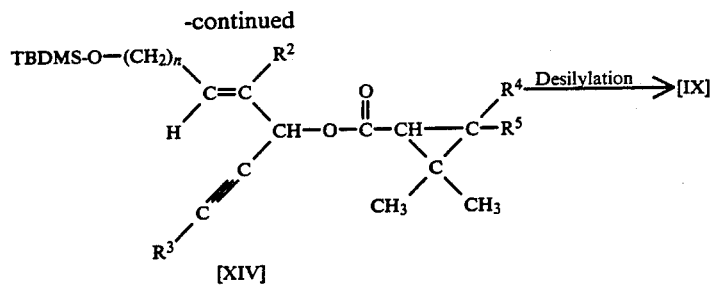

wherein TBDMS represents a tert-butyldimethylsilyl group, and n, z, $R^2$, $R^3$, $R^4$ and $R^5$ represent the same meanings as described above.

The reaction route described above will be explained in detail. Triethyl 2-fluoro-2-phosphonoacetate or triethyl 2-phosphonopropionate represented by the formula (IV) is converted to an unsaturated ester compound represented by the formula (XI) by reacting it firstly with a base (e.g. lithium diisopropylamide, sodium hydride) in an inert solvent (e.g. tetrahydrofuran, dimethylformamide) at a temperature of from $-80°$ to $30°$ C. for from 1 to 3 hours and then with a silyloxyaldehyde compound represented by the formula (X) [e.g. 3-(tert-butyldimethylsilyloxy)propionaldehyde, 4-(tert-butylsilyloxy)butyraldehyde] at a temperature of from $-70°$ to $30°$ C. for from 5 to 20 hours. This unsaturated ester compound is converted to an aldehyde compound represented by the formula (XII) by reacting it with a reducing agent (e.g. diisobutylaluminum hydride) in an inert solvent (e.g. toluene, hexane, diethyl ether) at a temperature of from $-70°$ to $60°$ C. for from 30 minutes to 2 hours. The aldehyde compound thus obtained is usually a mixture of E-form and Z-form geometrical isomers, but by treating it in an inert solvent (e.g. toluene, benzene, hexane, methylene chloride, diphenylsulfide with benzoylperoxide) at a temperature of from $30°$ to $110°$ C. for from 3 to 60 hours in the presence of an isomerization catalyst (e.g. sodium salt of thiophenol, iodine), it can be isomerized so as to contain a larger proportion of the geometrical isomer which is useful to produce the present compounds. Next, this aldehyde compound is converted to an alcohol compound represented by the formula (XIII) by reacting it with ethynylmagnesium bromide or 1-propynylmagnesium bromide at a temperature of from $0°$ to $40°$ C. for from 5 to 20 hours. This alcohol compound is converted to an ester compound represented by the formula (XIV) by reacting it with a carboxylic acid halide represented by the formula (III) (usually carboxylic acid chloride) in an inert solvent (e.g. toluene, benzene, hexane, diethyl ether) at a temperature of from $0°$ to $100°$ C. for from 30 minutes to 20 hours in the presence of a base (e.g. pyridine, triethylamine). The ester compound thus obtained is converted to the compound represented by the formula (IX) by reacting it with a desilylating agent (e.g. tetrabutylammonium fluoride, cesium fluoride) in an inert solvent (e.g. tetrahydrofuran, dimethylformamide, dimethyl sulfoxide) at a temperature of from $0°$ to $50°$ C. for from 30 minutes to 10 hours.

For the compound of the formula (IX) thus obtained, there are given for example the followings:

4-Fluoro-7-hydroxy-4-hepten-1-yne-3-yl 2,2-dimethyl-3-(2,2-dichlorovinyl)cyclopropane-1-carboxylate
4-Fluoro-7-hydroxy-4-hepten-1-yne-3-yl 2,2-dimethyl-3-(2,2-dibromovinyl)cyclopropane-1-carboxylate
4-Fluoro-7-hydroxy-4-hepten-1-yne-3-yl 2,2-dimethyl-3-(2-methyl-1-propenyl)cyclopropane-1-carboxylate
4-Fluoro-7-hydroxy-4-hepten-1-yne-3-yl 2,2,3,3-tetramethylcyclopropane-1-carboxylate
7-Hydroxy-4-methyl-4-hepten-1-yne-3-yl 2,2-dimethyl-3-(2,2-dichlorovinyl)cyclopropane-1-carboxylate
4-Fluoro-6-hydroxy-4-hexen-1-yne-3-yl 2,2-dimethyl-3-(2,2-dichlorovinyl)cyclopropane-1-carboxylate
4-Fluoro-8-hydroxy-4-octen-1-yne-3-yl 2,2-dimethyl-3-(2,2-dichlorovinyl)cyclopropane-1-carboxylate
5-Fluoro-8-hydroxy-5-octen-2-yne-4-yl 2,2-dimethyl-3-(2,2-dichlorovinyl)cyclopropane-1-carboxylate
4-Fluoro-9-hydroxy-4-nonen-1-yne-3-yl 2,2-dimethyl-3-(2,2-dichlorovinyl)cyclopropane-1-carboxylate The present invention will be illustrated in more detail with reference to the following production examples, reference examples, formulation examples and test examples, but it is not limited to these examples.

First, production examples of the present compounds will be shown.

PRODUCTION EXAMPLE 1

Production of the present compound (8)

220 Milligrams of 7-chloro-4-fluoro-3-hydroxy-4-hepten-1-yne and 307 mg of (1RS)-trans-2,2-dimethyl-3-(2,2-dichlorovinyl)cyclopropane-1-carboxylic acid chloride were dissolved in 5 ml of dry toluene, and to the resulting solution was added dropwise 320 mg of pyridine with ice-cooling. After addition, the solution was stirred at room temperature for 10 hours. The reaction solution was poured into 5 ml of cooled 5% aqueous hydrochloric acid, and the toluene layer was separated. The aqueous layer was extracted twice with ether, and the ether extracts were combined with the above toluene layer. This mixture was successively washed with water and a saturated aqueous sodium chloride solution, dried over anhydrous magnesium sulfate, and the solvent was removed under reduced pressure. The residue obtained was treated by column chromatography on silica gel with an ethyl acetate/hexane (1:20) mixture as an eluent to obtain 280 mg of the desired compound as a colorless oily product (yield, 59.1% based on the carboxylic acid chloride).

NMR data (solvent, deutero chloroform; internal standard, TMS):

$\delta$(ppm) 1.21 (s, 3H), 1.31 (s, 3H), 1.67 (d, 1H), 2.28 (dd, 1H), 2.43~2.85 (m, 2H), 2.61 (d, 1H), 3.56 (t, 2H), 5.36 (dt, 1H), 5.61 (d, 1H), 5.97 (bd, 1H)

PRODUCTION EXAMPLE 2

Production of the present compound (14)

710 Milligrams of 6,6,6-trifluoro-3-hydroxy-4-methyl-4-hexen-1-yne and 920 mg of (1RS)-trans-2,2-dimethyl-3-(2,2-dichlorovinyl)cyclopropane-1-carboxylic acid chloride were dissolved in 10 ml of dry toluene, and to the resulting solution was added dropwise 640 mg of pyridine with ice-cooling. After addition, the solution was stirred at room temperature for 10 hours. Thereafter, the same work up as in Example 1 was carried out to obtain 810 mg of the desired compound as a colorless oily product (yield, 56.5% based on the carboxylic acid chloride).

NMR data (solvent, deutero chloroform; internal standard, TMS):

δ(ppm) 1.23 (s, 3H), 1.29 (s, 3H), 1.59~1.81 (m, 1H), 2.00 (bs, 3H), 2.13~2.48 (m, 1H), 2.66 (d, 1H), 5.35~6.47 (m, 1H), 5.70 (d, 1H), 5.90 (bs, 1H)

PRODUCTION EXAMPLE 3

Production of the present compound (17)

390 Milligrams of 6,6,7,7,7-pentafluoro-3-hydroxy-4-methyl-4-hepten-1-yne and 390 mg of (1RS)-trans-2,2-dimethyl-3-(2,2-dichlorovinyl)cyclopropane-1-carboxylic acid chloride were dissolved in 10 ml of dry toluene, and to the resulting solution was added dropwise 420 mg of pyridine with ice-cooling. After addition, the solution was stirred at room temperature for 10 hours. Thereafter, the same work up as in Example 1 was carried out to obtain 470 mg of the desired compound as a colorless oily product (yield, 67.8% based on the carboxylic acid chloride).

NMR data (solvent, deutero chloroform; internal standard, TMS):

δ(ppm) 1.21 (s, 3H), 1.29 (s, 3H), 1.57~1.79 (m, 1H), 2.00 (bs, 3H), 2.11~2.48 (m, 1H), 2.58 (d, 1H), 5.21~6.47 (m, 1H), 5.57 (d, 1H), 5.80 (bs, 1H)

PRODUCTION EXAMPLE 4

Production of the present compound (20)

1.72 Grams of 8-chloro-4-fluoro-3-hydroxy-4-octen-1-yne and 2.20 g of (1RS)-cis,trans-2,2-dimethyl-3-(2,2-dichlorovinyl)cyclopropane-1-carboxylic acid chloride were dissolved in 20 ml of dry toluene, and to the resulting solution was added dropwise 1.94 g of pyridine with ice-cooling. After addition, the solution was stirred at room temperature for 10 hours. Thereafter, the same work up as in Example 1 was carried out to obtain 2.51 g of the desired compound as a colorless oily product (yield, 70.6% based on the carboxylic acid chloride).

NMR data (solvent, deutero chloroform; internal standard, TMS):

δ(ppm) 1.14~1.38 (m, 6H), 1.49~2.44 (m, 6H), 2.55 (d, 1H), 3.49 (t, 2H), 5.20 (dt, 1H), 5.47~6.27 (m, 1H), 5.87 (bd, 1H)

PRODUCTION EXAMPLE 5

Production of the present compound (33)

One hundred milligrams of 4,6,6,6-tetrafluoro-3-hydroxy-4-hexen-1-yne and 134 mg of (1R)-trans-2,2-dimethyl-3-(2,2-dichlorovinyl)cyclopropane-1-carboxylic acid chloride were dissolved in 3 ml of dry toluene, and to the resulting solution was added dropwise 120 mg of pyridine with ice-cooling.

After addition, the solution was stirred at room temperature for 10 hours. Thereafter, the same work up as Example 1 was carried out to obtain 90 mg of the desired compound as a colorless oily product (yield, 42.6%).

NMR data (solvent, deutero chloroform; internal standard, TMS):

δ(ppm) 1.23 (s, 3H), 1.29 (s, 3H), 1.68 (d, 1H), 2.30 (dd, 1H), 2.67 (d, 1H), 5.63 (d, 1H), 5.68 (dq, 1H), 5.95~6.11 (m, 1H)

PRODUCTION EXAMPLE 6

Production of the present compound (1)

920 Milligrams of 4-fluoro-7-hydroxy-4-hepten-1-yne-3-yl (1R)-trans-2,2-dimethyl-3-(2,2-dichlorovinyl)-cyclopropane-1-carboxylate was dissolved in 10 ml of dry methylene chloride. The resulting solution was cooled to −50° C. in a dry ice-acetone bath, and 0.27 ml of diethylaminosulfur trifluoride was added dropwise by means of an injector. After 30 minutes, the temperature was raised to 0° C. in an ice bath, and the solution was stirred for further 2 hours. Thereafter, 10 ml of water was added, and the methylene chloride layer was separated. The aqueous layer was extracted twice with methylene chloride, and the extracts were combined with the above methylene chloride layer. This mixture was washed with a saturated aqueous sodium chloride solution, dried over anhydrous magnesium sulfate, and the solvent was removed under reduced pressure. The residue obtained was treated by column chromatography on silica gel with a hexane/benzene/chloroform (6:6:1) mixture as an eluent to obtain 270 mg of the desired compound as a colorless oily product (yield, 29.1%).

NMR data (Solvent, deutero chloroform; internal standard, TMS):

δ(ppm) 1.22 (s, 3H), 1.31 (s, 3H), 1.69 (d, 1H), 2.17~2.99 (m, 2H), 2.30 (dd, 1H), 2.61 (d, 1H), 4.45 (dt, 2H), 5.34 (dt, 1H), 5.59 (d, 1H), 5.97 (bd, 1H)

Examples of the present compound obtained in the same manner as above will be shown in Table 1.

TABLE 1

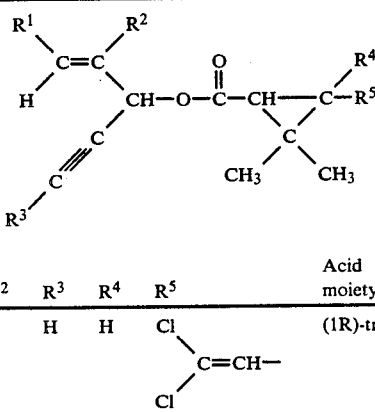

| Compound No. | R¹ | R² | R³ | R⁴ | R⁵ | Acid moiety | Alcohol moiety | Refractive index (°C.) |
|---|---|---|---|---|---|---|---|---|
| (1) | FCH$_2$CH$_2$ | F | H | H | Cl\C=CH—/Cl | (1R)-trans | (±) | 1.4958 (19.6) |

TABLE 1-continued

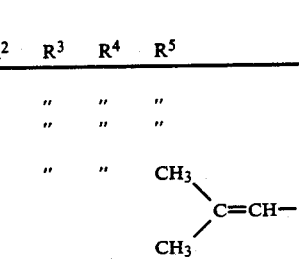

| Compound No. | R¹ | R² | R³ | R⁴ | R⁵ | Acid moiety | Alcohol moiety | Refractive index (°C.) |
|---|---|---|---|---|---|---|---|---|
| (2) | " | " | " | " | " | (1RS)-trans | (±) | 1.4898 (20.0) |
| (3) | " | " | " | " | " | (1R)-cis | (±) | 1.4990 (19.0) |
| (4) | " | " | " | " | $\mathrm{CH_3} \atop \mathrm{CH_3}$>C=CH— | (1R)-cis, trans | (±) | 1.4702 (20.3) |
| (5) | " | " | " | " | $\mathrm{Br} \atop \mathrm{Br}$>C=CH— | (1R)-cis | (±) | 1.5210 (23.0) |
| (6) | FCH₂CH₂ | F | H | H | $\mathrm{CF_3} \atop \mathrm{Cl}$>C=CH— | (1R)-cis | (±) | 1.4593 (20.0) |
| (7) | " | " | " | CH₃ | CH₃ | — | (±) | 1.4642 (22.0) |
| (8) | ClCH₂CH₂ | " | " | H | $\mathrm{Cl} \atop \mathrm{Cl}$>C=CH— | (1RS)-trans | (±) | 1.5088 (21.5) |
| (9) | " | " | " | " | $\mathrm{CH_3} \atop \mathrm{CH_3}$>C=CH— | (1R)-cis, trans | (±) | 1.4832 (21.0) |
| (10) | " | " | " | " | $\mathrm{CF_3} \atop \mathrm{Cl}$>C=CH— | (1RS)-cis | (±) | 1.4560 (23.0) |
| (11) | " | " | " | " | $\mathrm{Br} \atop \mathrm{Br}$>C=CH— | (1R)-cis | (±) | 1.5332 (20.0) |
| (12) | " | " | " | " | $\mathrm{F} \atop \mathrm{F}$>C=CH— | (1R)-trans | (±) | 1.4583 (22.0) |
| (13) | CF₃ | CH₃ | H | H | $\mathrm{CH_3} \atop \mathrm{CH_3}$>C=CH— | (1R)-cis, trans | (±) | 1.4523 (22.0) |
| (14) | " | " | " | " | $\mathrm{Cl} \atop \mathrm{Cl}$>C=CH— | (1RS)-trans | (±) | 1.4708 (22.3) |
| (15) | " | " | " | " | $\mathrm{Br} \atop \mathrm{Br}$>C=CH— | (1R)-cis | (±) | 1.4928 (22.0) |

TABLE 1-continued

[Structure: R¹R²C=CH-C(R³)=... CH-O-C(=O)-CH-C(CH₃)(CH₃)-C-R⁴R⁵ cyclopropane structure]

| Compound No. | R¹ | R² | R³ | R⁴ | R⁵ | Acid moiety | Alcohol moiety | Refractive index (°C.) |
|---|---|---|---|---|---|---|---|---|
| (16) | " | " | " | " | CF₃\C=CH— /Cl | (1RS)-cis | (±) | 1.4383 (19.6) |
| (17) | CF₃CF₂ | " | " | " | Cl\C=CH— /Cl | (1RS)-trans | (±) | 1.4598 (24.5) |
| (18) | " | " | " | " | Br\C=CH— /Br | (1R)-trans | (±) | 1.4923 (22.0) |
| (19) | CF₃CF₂CF₂ | CH₃ | H | H | Cl\C=CH— /Cl | (1RS)-trans | (±) | 1.4502 (24.7) |
| (20) | ClCH₂CH₂CH₂ | F | " | " | " | (1RS)-cis, trans | (±) | 1.5081 (23.5) |
| (21) | FCH₂CH₂ | CH₃ | " | " | " | (1RS)-trans | (±) | 1.5029 (23.5) |
| (22) | FCH₂ | " | " | " | " | (1R)-trans | (±) | 1.5003 (25.5) |
| (23) | FCH₂CH₂CH₂ | F | " | " | " | (1RS)-trans | (±) | 1.4952 (20.5) |
| (24) | FCH₂CH₂ | " | CH₃ | " | " | (1R)-trans | (±) | 1.5002 (20.0) |
| (25) | CF₃ | CH₃ | " | " | " | (1R)-trans | (±) | 1.4722 (21.0) |
| (26) | CH₃ | " | H | CH₃ | CH₃ | — | (±) | 1.4554 (22.0) |
| (27) | FCH₂CH₂ | F | H | H | Cl\C=CH— /Cl | (1R)-trans | (−) | 1.4952 (20.0) |
| (28) | CF₃ | CH₃ | " | " | " | (1R)-trans | (−) | 1.4792 (20.0) |
| (29) | FCH₂CH₂ | F | " | " | " | (1RS)-cis, trans | (±) | 1.4972 (21.3) |
| (30) | " | " | " | " | " | (1RS)-cis | (±) | 1.4952 (23.3) |
| (31) | ClCH₂CH₂ | " | " | " | " | (1RS)-cis, trans | (±) | 1.4972 (23.5) |
| (32) | BrCH₂ | " | " | " | " | (1RS)-cis, trans | (±) | 1.5229 (19.5) |
| (33) | CF₃ | " | " | " | " | (1R)-trans | (±) | 1.4658 (20.2) |
| (34) | CF₃CF₂ | " | " | " | " | (1R)-trans | (±) | 1.4492 (23.0) |
| (35) | CF₃CF₂CF₂ | " | " | " | " | (1R)-trans | (±) | 1.4339 (22.5) |

Next, production of the compounds, a material, used to produce the present compounds will be shown in the reference examples.

REFERENCE EXAMPLE 1

Production of 8-chloro-4-fluoro-3-hydroxy-4-octen-1-yne (i) Production of ethyl (E)-6-chloro-2-fluoro-2-hexenoate Ethyl (E)-6-chloro-2-fluoro-2-hexenoate was produced using 4-chlorobutyraldehyde according to Horner-Emmons reaction with triethyl 2-fluoro-2-phosphonoacetate described in J. Am. Chem. Soc., Vol. 103, pp. 7195, 1981.

NMR data (solvent, deutero chloroform; internal standard, TMS):

δ(ppm) 1.32 (t, 3H), 1.86 (q, 2H), 2.38~2.85 (m, 2H), 3.48 (t, 2H), 4.18 (q, 2H), 5.75 (dt, 1H)

(ii) Production of 6-chloro-2-fluoro-2-hexenal 4.56 Grams of ethyl (E)-6-chloro-2-fluoro-2-hexenoate was dissolved in 50 ml of hexane under a nitrogen atmosphere. The resulting solution was cooled to −78° C. in a dry ice-acetone bath, and 24 ml of diisobutylaluminum hydride (as 1.0 M hexane solution) was added dropwise. After addition, the solution was stirred at −78° C. for 1 hour. The reaction solution was poured into cooled 5% hydrochloric acid, and after separating the hexane layer, the aqueous layer was extracted twice with ether. The ether extracts were combined with the above hexane layer, and this mixture was washed with a saturated aqueous sodium chloride solution and dried over anhydrous magnesium sulfate. The solvent was then removed under reduced pressure to obtain 2.35 g of 6-chloro-2-fluoro-2-hexenal [E form/Z form (6.8:1) mixture by NMR determination].

NMR data (solvent, deutero chloroform; internal standard, TMS):

δ(ppm) 1.72~2.23 (m, 2H), 2.44~2.97 (m, 2H), 3.61 (t, 2H), 5.96 (Z form) and 6.18 (E form) (dt, 1H), 9.21 (Z form) and 9.79 (E form) (d, 1H).

(iii) Production of (Z)-6-chloro-2-fluoro-2-hexenal 2.35 Grams of 6-chloro-2-fluoro-2-hexenal (E form : Z form =6.8 : 1) was dissolved in 20 ml of dry toluene, and after adding 10 mg of the sodium salt of thiophenol, the resulting solution was heated under reflux for 25 hours with stirring. Thereafter, 10 ml of water was added to the reaction solution, and the toluene layer was separated. The aqueous layer was extracted twice with ether, and the ether extracts were combined with the above toluene layer. This mixture was washed with a saturated aqueous sodium chloride solution and dried over anhydrous magnesium sulfate. The solvent was removed under reduced pressure to obtain 2.35 g of (Z)-6-chloro-2-fluoro-2-hexenal.

(iv) Production of 8-chloro-4-fluoro-3-hydroxy-4-octen-1-yne 2.35 Grams of (Z)-6-chloro-2-fluoro-2-hexenal was dissolved in 20 ml of dry tetrahydrofuran, and to the resulting solution was added dropwise a tetrahydrofuran solution of ethynylmagnesium bromide (1.5 equivalents vs. the aldehyde) with ice-cooling. After addition, the solution was stirred at room temperature for 10 hours. The reaction solution was cooled with ice, and after adding 50 ml of ether, poured into 10% hydrochloric acid. The ether layer was separated, and the aqueous layer was extracted twice with ether. The ether extracts were combined with the above ether layer, and this mixture was washed with a saturated aqueous sodium chloride solution and dried over anhydrous magnesium sulfate. The solvent was then removed under reduced pressure. The residue obtained was treated by column chromatography on silica gel with an ethyl acetate/hexane (1:5) mixture as an eluent to obtain 1.72 g of 8-chloro-4-fluoro-3-hydroxy-4-octen-1-yne as a pale yellow oily product.

NMR data (solvent, deutero chloroform; internal standard, TMS):

δ(ppm) 1.60~2.55 (m, 4H), 2.64 (d, 1H), 3.58 (t, 2H), 3.86 (bs, 1H), 4.72~5.16 (m, 1H), 5.19 (dt, 1H)

REFERENCE EXAMPLE 2

Production of 4-fluoro-7-hydroxy-4-hepten-1-yne-3-yl (1R)-trans-2,2-dimethyl-3-(2,2-dimethyl-3-(2,2-dichlorovinyl)cyclopropane-1-carboxylate (i) Production of ethyl (E)-2-fluoro-5-(tertbutyldimethylsilyloxy)-2-pentenoate Ethyl (E)-2-fluoro-5-(tert-butyldimethylsilyloxy)-2-pentenoate was produced using 3-(tertbutyldimethylsilyloxy)propionaldehyde according to Horner-Emmons reaction with triethyl 2-fluoro-2-phosphonoacetate described in J. Am. Chem. Soc., Vol. 103, pp. 7195, 1981.

NMR data (solvent, deutero chloroform; internal standard, TMS):

δ(ppm) 0.05 (s, 6H), 0.90 (s, 9H), 1.32 (t, 3H), 2.48~2.97 (m, 2H), 3.70 (t, 2H), 4.28 (q, 2H), 5.99 (dt, 1H)

(ii) Production of 2-fluoro-5-(tert-butyldimethylsilyloxy)-2-pentenal 6.91 Grams of ethyl (E)-2-fluoro-5-(tertbutyldimethylsilyloxy)-2-pentenoate was dissolved in 50 ml of hexane under a nitrogen atmosphere. The resulting solution was cooled to −78° C. in a dry ice-acetone bath, and 26 ml of diisobutylaluminum hydride (as 1.0 M hexane solution) was added dropwise. After addition, the solution was stirred at −78° C. for 1 hour. The reaction solution was poured into cooled 5% hydrochloric acid, and after separating the hexane layer, the aqueous layer was extracted twice with ether. The ether extracts were combined with the above hexane layer, and this mixture was washed with a saturated aqueous sodium chloride solution and dried over anhydrous magnesium sulfate. The solvent was then removed under reduced pressure to obtain 5.50 g of 2-fluoro-5-(tert-butyldimethylsilyloxy)-2-pentenal [E form/Z form (11:1) mixture by NMR determination].

NMR data (solvent, deutero chloroform; internal standard, TMS):

δ(ppm) 0.05 (s, 6H), 0.89 (s, 9H), 2.42~2.94 (m, 2H), 3.74 (t, 2H), 6.02 (Z form) and 6.32 (E form) (dt, 1H), 9.19 (Z form) and 9.70 (E form) (d, 1H).

(iii) Production of (Z)-2-fluoro-5-(tert-butyldimethylsilyloxy)-2-pentenal 5.50 Grams of 2-fluoro-5-(tert-butyldimethylsilyloxy)-2-pentenal (E form:Z form=11:1) was dissolved in 50 ml of dry hexane, and after adding 20 mg of the sodium salt of thiophenol, the resulting solution was heated under reflux for 20 hours with stirring. Thereafter, 10 ml of water was added to the reaction solution, and the toluene layer was separated. The aqueous layer was extracted twice with ether, and the ether extracts were combined with the above toluene layer. This mixture was washed with a saturated aqueous sodium chloride solution and dried over anhydrous magnesium sulfate. The solvent was removed under reduced pressure to obtain 5.50 g of (Z)-2-fluoro-5-(tert-butyldimethylsilyloxy)-2-pentenal.

(iv) Production of 7-(tert-butyldimethylsilyloxy)-4-fluoro-3-hydroxy-4-hepten-1-yne 5.01 Grams of (Z)-2-fluoro-5-(tert-butyldimethylsilyloxy)-2-pentenal was dissolved in 20 ml of dry tetrahydrofuran, and to the resulting solution was added dropwise a tetrahydrofuran solution of ethynylmagnesium bromide (1.5 equivalents vs. the aldehyde) with ice-cooling. After addition, the solution was stirred at room temperature for 10 hours. The reaction solution was cooled with ice, and after adding 50 ml of ether, poured into 10% hydrochloric acid. The ether layer was separated, and the aqueous layer was extracted twice with ether. The ether extracts were combined with the above ether layer, and this mixture was washed with a saturated aqueous sodium chloride solution and dried over anhydrous magnesium sulfate. The solvent was then removed under reduced pressure. The residue obtained was treated by column chromatography on silica gel with an ethyl acetate/hexane (1:5) mixture as an eluent to obtain 3.42 g of 7-(tert-butyldimethylsilyloxy)-4-fluoro-3-hydroxy-4-hepten-1-yne as a pale yellow oily product.

NMR data (solvent, deutero chloroform; internal standard, TMS):

δ(ppm) 0.06 (s, 6H), 0.91 (s, 9H), 2.13~2.56 (m, 2H), 2.58 (d, 1H), 2.89 (bd, 1H), 3.66 (t, 2H), 4.63~5.12 (m, 1H), 5.24 (dt, 1H)

(v) Production of 7-(tert-butyldimethylsilyloxy)-4-fluoro-4-hepten-1-yne-3-yl (1R)-trans-2,2-dimethyl-3-(2,2-dichlorovinyl)cyclopropane-1-carboxylate 1.50 Grams of 7-(tert-butyldimethylsilyloxy)-4-fluoro-3-hydroxy-4-hepten-1-yne and 1.31 g of (1R)-trans-2,2-dimethyl-3-(2,2-dichlorovinyl)cyclopropane-1-carboxylic acid chloride were dissolved in 10 ml of dry toluene, and to the resulting solution was added dropwise 1.13 g of pyridine with ice-cooling. After addition, the solution was stirred at room temperature for 10 hours. The reaction solution was poured into 10 ml of cooled 5% hydrochloric acid, and the toluene layer was separated. The aqueous layer was extracted twice with ether, and the ether extracts were combined with the above toluene layer. This mixture was successively washed with water and a saturated aqueous sodium chloride solution and dried over anhydrous magnesium sulfate. The solvent was then removed under reduced pressure. The residue obtained was treated by column chromatography on silica gel with an ethyl acetate/hexane (1:10) mixture as an eluent to obtain 1.72 g of the desired compound as a colorless oily product.

NMR data (solvent, deutero chloroform; internal standard, TMS):

δ(ppm) 0.07 (s, 6H), 0.92 (s, 9H), 1.20 (s, 3H), 1.30 (s, 3H), 1.69 (d, 1H), 2.10~2.58 (m, 3H), 2.58 (d, 1H), 3.68 (t, 2H), 5.37 (dt, 1H), 5.61 (d, 1H), 5.97 (bd, 1H)

(vi) Production of 4-fluoro-7-hydroxy-4-hepten-1-yne-3-yl (1R)-trans-2,2-dimethyl-3-(2,2-dichlorovinyl)cyclopropane-1-carboxylate 1.72 Grams of 7-(tert-butyldimethylsilyloxy)-4-fluoro-4-hepten-1-yne-3-yl (1R)-trans-2,2-dimethyl-3(2,2-dichlorovinyl)cyclopropane-1-carboxylate was dissolved in 20 ml of dry tetrahydrofuran, and to the resulting solution was added dropwise 3.9 ml of tetra-n-butylammonium fluoride (as 1.0 M tetrahydrofuran solution) with ice-cooling. After addition, the solution was stirred for 1 hour with ice-cooling, and 20 ml of ether and 20 ml of ice water were added. The ether layer was separated, and the aqueous layer was extracted three times with ether. The ether extracts were combined with the above ether layer, and this mixture was washed with a saturated aqueous sodium chloride solution and dried over anhydrous magnesium sulfate. The solvent was then removed under reduced pressure. The residue obtained was treated by column chromatography on silica gel with an ethyl acetate/hexane (1:1) mixture as an eluent to obtain 920 mg of the desired compound as a colorless oily product.

NMR data (solvent, deutero chloroform; internal standard, TMS):

δ(ppm) 1.20 (s, 3H), 1.30 (s, 3H), 1.67 (d, 1H), 2.19~2.67 (m, 3H), 2.29 (dd, 1H), 2.60 (d, 1H), 3.70 (t, 2H), 5.37 (dt, 1H), 5.61 (d, 1H), 5.99 (bd, 1H)

(vii) Production of (Z)-4,6,6,6-tetrafluoro-3-hydroxy-4-hexen-1-yne

To the solution of 2,4,4,4-tetrafluoro-2-butenol (1.40 g) and anhydrous sodium acetate (60 mg) in methylene chloride (5 ml) was added in portionwise pyridinium chlorochromate (3.23 g) at 20° C. The resulting mixture was stirred for 12 hours. The mixture was passed through a short silica gel column with dry ether (20 ml) to obtain the ether solution of (Z)-2,4,4,4-tetrafluoro-2-butenal. Without evaporation, a tetrahydrofuran solution of ethynylmagnesium bromide (21 ml) was added portionwise to the solution of (Z)-2,4,4,4-tetrafluoro-2-butenal at 0° C. The resulting mixture was stirred for 12 hours at 20° C. This was poured into the cooled 5% hydrochloric acid, and the resulting mixture was extracted with ether. The ether extract was washed with a saturated aqueous sodium chloride solution and dried over anhydrous magnesium sulfate.

The solvent was evaporated in vacuo to give the crude alcohol, which was purified by silica gel column chromatography eluted with ethyl acetate/hexane (1:5) mixture to obtain 0.48 g of 4,6,6,6-tetrafluoro-3-hydroxy-4-hexen-1-yne.

NMR data (solvent, deutero chloroform; internal standard, TMS):

δ(ppm) 2.64 (d, 1H), 4.56 (bs, 1H), 4.96 (bd, 1H) 5.61 (dq. 1H)

When the present compounds are used as an active ingredient for insecticides, they may be used as they are without adding any other ingredients. Usually, however, they are formulated into emulsifiable concentrates, wettable powders, dusts, granules, oil sprays, aerosols, heating fumigants (e.g. mosquito coils, electric mosquito mats, porous ceramic plates), foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carriers, mats, etc.

In these preparations, the content of the present compounds, which are an active ingredient, is from 0.001% to 95% by weight. The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. benzene, toluene, xylene, methylnaphthalene), halogenated hydrocarbons (e.g. dichloroethane, trichloroethylene, carbon tetrachloride), alcohols (e.g. ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (Liquefied petroleum gas), dimethyl ether and the like. The surface active agent used for emulsification, dispersion, wetting, etc. includes for example anionic surface active agents such as the salt of alkyl sulfates, alkyl(aryl)sulfonates, dialkyl sulfosuccinates, the salt of polyoxyethylene alkylaryl ether phosphoric acid esters, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as fixing agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [eg. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate) and the like.

Next, formulation examples will be shown. In the examples, parts are by weight.

FORMULATION EXAMPLE 1

0.2 Part of each of the present compounds (1) to (35), 2 parts of xylene and 97.8 parts of deodorized kerosene are mixed to obtain an oil spray of each compound.

FORMULATION EXAMPLE 2

Ten parts of each of the present compounds (1) to (35), 14 parts of polyoxyethylene styrylphenyl ether, 6 parts of calcium dodecylbenzenesulfonate and 70 parts of xylene are well mixed to obtain an emulsifiable concentrate of each compound.

FORMULATION EXAMPLE 3

Twenty parts of each of the present compounds (1), (8) and (13), 10 parts of fenitrothion, 3 parts of calcium lignosulfonate, 2 parts of sodium lauryl sulfate and 65 parts of synthetic hydrated silicon dioxide are well pulverized and mixed to obtain a wettable powder of each compound.

FORMULATION EXAMPLE 4

One part of each of the present compounds (2), (9) and (14), 2 parts of carbaryl, 87 parts of kaolin clay and 10 parts of talc are well pulverized and mixed to obtain a dust of each compound.

FORMULATION EXAMPLE 5

Five parts of each of the present compounds (3), (10) and (15), 1 part of synthetic hydrated silicon dioxide, 2 parts of calcium lignosulfonate, 30 parts of bentonite and 62 parts of kaolin clay are well pulverized and mixed, and the resulting mixture is well kneaded with water, granulated and dried to obtain a granule of each compound.

FORMULATION EXAMPLE 6

0.05 Part of each of the present compounds (4), (11) and (16), 0.2 part of tetramethrin, 0.05 part of resmethrin, 7 parts of xylene and 32.7 parts of deodorized kerosene are mixed into a solution and filled in an aerosol container. After attaching a valve portion to the container, 60 parts of a propellant (liquefied petroleum gas) is charged to the container through the valve portion under pressure to obtain an aerosol of each compound.

FORMULATION EXAMPLE 7

0.6 Gram of each of the present compounds (1) to (35) is dissolved in 20 ml of methanol, and each solution is uniformly mixed with stirring with 99.4 g of a mosquito coil carrier containing tabu powder, pyrethrum marc and wood powder in a proportion of 3:5:1. After vaporizing methanol, 150 ml of water is added to the residue, and the mixture is well kneaded, shaped and dried to obtain a mosquito coil of each compound.

FORMULATION EXAMPLE 8

One hundred milligrams of each of the present compounds (1) to (35) is dissolved in a suitable amount of acetone and impregnated into a porous ceramic plate of 4.0 cm×4.0 cm×1.2 cm (thick) to obtain a heating fumigant of each compound.

FORMULATION EXAMPLE 9

Five hundred milligrams of each of the present compounds (1) to (35) is dissolved in a suitable amount of acetone and uniformly coated onto a filter paper of 10 cm×15 cm×0.28 mm (thick). Acetone is then air-dried to obtain a room-temperature volatile formulation of each compound.

These preparations are used as they are or diluted with water. Also, they may be used in mixture with other insecticides, acaricides, nematocides, fungicides, herbicides, plant growth regulators, fertilizers, soil improvers, etc.

When the present compounds are used as agricultural insecticides, their dosage rate is usually from 5 g to 500 g per 10 ares. When emulsifiable concentrates, wettable powders, etc. are used diluted with water, the application concentration of the present compounds is from 10 ppm to 1000 ppm, and dusts, granules, etc. are used as they are without dilution.

When the present compounds are used as household or hygienic insecticides, emulsifiable concentrates, wettable powders, etc. are applied in dilution with water to from 10 ppm to 10000 ppm. Also, oil sprays, aerosols, fumigants (e.g. mosquito coils, electric mats) and volatile formulations are applied as they are.

TABLE 2

| Compound symbol | Structural formula | Remark |
|---|---|---|
| (A) | $\begin{array}{c} CH_3O \\ \phantom{CH_3O} \diagdown \\ \phantom{CH_3O} \phantom{\diagdown} P-S-CHCOOC_2H_5 \\ \phantom{CH_3O} \diagup \phantom{P-S-} | \\ CH_3O \phantom{\diagup} \phantom{P-S-} CH_2COOC_2H_5 \end{array}$ | Malathion |
| (B) | (structural formula) | Compound No. 38 described in JP-B-55-42045. |
| (C) | (structural formula) | Compound No. 74 described in the same patent as above. |

TABLE 2-continued

| Compound symbol | Structural formula | Remark |
|---|---|---|
| (D) | | Allethrin |
| (E) | | Compound No. 1 described in GB-A-2174700. |
| (F) | | Compound No. 7 described in GA-A-2174700. |

*(1R)-trans-form in the acid moiety

TEST EXAMPLE 1

The emulsifiable concentrates of the following present compounds obtained according to Formulation example 2 were each diluted with water to a concentration of 3.5 ppm. One hundred milliliters of the dilute solution was put in a 180-ml polyethylene cup, and 20 last instar larvae of common mosquito (*Culex pipiens pallens*) were liberated therein. Next day, the dead and alive were examined to obtain mortality (two replications).

The results are shown in Table 3.

TABLE 3

| Test compound | Mortality (%) | Test compound | Mortality (%) |
|---|---|---|---|
| (1) | 100 | (19) | 100 |
| (2) | 100 | (20) | 100 |
| (3) | 100 | (21) | 100 |
| (4) | 100 | (22) | 100 |
| (5) | 100 | (23) | 100 |
| (6) | 100 | (24) | 100 |
| (7) | 100 | (25) | 100 |
| (8) | 100 | (26) | 100 |
| (9) | 100 | (27) | 100 |
| (10) | 100 | (28) | 100 |
| (11) | 100 | (29) | 100 |
| (12) | 100 | (30) | 100 |
| (13) | 100 | (31) | 100 |
| (14) | 100 | (32) | 100 |
| (15) | 100 | (33) | 100 |
| (16) | 100 | (34) | 100 |
| (17) | 100 | (35) | 100 |
| (18) | 100 | No treatment | 0 |

TEST EXAMPLE 2

Rice seedlings (about 12 cm in length) were dipped for 1 minute in the 200-fold aqueous dilute solutions (corresponding to 500 ppm) of the emulsifiable concentrates of the following present compounds and controls obtained according to Formulation example 2. After air-drying, the rice seedlings were put in a test tube, and 10 adults of green rice leafhopper (*Nephotettix cincticeps*) of resistant strain were liberated in the tube. After one day, the dead and alive were examined to obtain mortality (two replications).

The results are shown in Table 4.

TABLE 4

| Test compound | Mortality (%) | Test compound | Mortality (%) |
|---|---|---|---|
| (1) | 100 | (19) | 85 |
| (2) | 90 | (20) | 100 |
| (3) | 100 | (21) | 100 |
| (4) | 100 | (22) | 100 |
| (5) | 100 | (23) | 100 |
| (6) | 100 | (24) | 100 |
| (7) | 100 | (25) | 100 |
| (8) | 100 | (26) | 95 |
| (9) | 100 | (27) | 100 |
| (10) | 100 | (28) | 100 |
| (11) | 100 | (29) | 100 |
| (12) | 100 | (30) | 100 |
| (13) | 100 | (31) | 100 |
| (14) | 100 | (32) | 100 |
| (15) | 100 | (33) | 100 |
| (16) | 100 | (34) | 100 |
| (17) | 100 | (35) | 90 |
| (18) | 100 | (A) | 50 |
|  |  | No treatment | 5 |

TEST EXAMPLE 3

Each of the following present compounds and controls was diluted with acetone and uniformly applied onto the bottom (bottom area, 63.6 cm²) of a glass Petri dish of 9 cm in inner diameter and 2 cm in height so that its dosage rate was 50 mg/m². After acetone was vaporized in air, this treated Petri dish was put as a cover on the top of a polyethylene cup (diameter, 9 cm; height, 4.5 cm), in which 20 female adults of susceptible housefly (*Musca domestica*, CSMA strain) were liberated, with a nylon net (16 mesh) therebetween so that the adults were not brought into direct contact with the treated surface of the Petri dish. After 120 minutes elapsed, the Petri dish was removed, and water and baits were given to the adults. After 24 hours, the dead and alive were examined to obtain mortality (two replications).

The results are shown in Table 5.

TABLE 5

| Test compound | Mortality (%) | Test compound | Mortality (%) |
|---|---|---|---|
| (1) | 100 | (24) | 100 |
| (2) | 100 | (25) | 100 |
| (3) | 100 | (26) | 100 |

TABLE 5-continued

| Test compound | Mortality (%) | Test compound | Mortality (%) |
|---|---|---|---|
| (4) | 100 | (27) | 100 |
| (5) | 100 | (28) | 100 |
| (6) | 100 | (29) | 100 |
| (7) | 100 | (30) | 100 |
| (13) | 100 | (33) | 100 |
| (14) | 100 | (B) | 3 |
| (16) | 100 | (C) | 25 |
| (17) | 100 | (D) | 5 |
| (21) | 100 | No treatment | 3 |
| (22) | 100 | | |
| (23) | 100 | | |

TEST EXAMPLE 4

Mosquito coils containing 0.6% of each of the present compounds and control were prepared according to Formulation example 7.

Ten female adults of common mosquito (*Culex pipiens pallens*) and ten adults of housefly (*Musca domestica*) (male:female=1:1) were liberated in a 70 cm-cube (0.34 m³) glass chamber.

One gram of each mosquito coil ignited at the both ends was put in this glass chamber, and the number of knocked-down insects was observed through the lapse of time. KT₅₀ values (50% knock-down time) were obtained by the Probit method (two replications).

The results are shown in Table 6.

TABLE 6

| Test compound | KT₅₀ value (minute) Housefly | Common Mosquito |
|---|---|---|
| (1) | 4.0 | 3.3 |
| (2) | 5.2 | 4.4 |
| (3) | 4.2 | 3.5 |
| (4) | 5.7 | 4.4 |
| (5) | 6.3 | 5.3 |
| (6) | 7.4 | 5.9 |
| (7) | 7.0 | 5.4 |
| (8) | 3.9 | 6.2 |
| (9) | 4.2 | 6.7 |
| (10) | 5.0 | 8.0 |
| (12) | 3.5 | ≈3 |
| (21) | 5.7 | 4.8 |
| (25) | 6.6 | 7.0 |
| (27) | 3.2 | ≦3 |
| (28) | 5.2 | 5.6 |
| (29) | 5.8 | 4.5 |
| (30) | 5.7 | 4.5 |
| (31) | 4.3 | 6.8 |
| (D) | 10 | 8.7 |

TEST EXAMPLE 5

Oil formulations containing 0.1% of each of the present compounds and controls were prepared according to Formulation example 1.

Ten female adults of common mosquito (*Culex pipiens pallens*) and ten adults of housefly (*Musca domestica*) (male:female=1:1) were liberated in a cm-cube (0.34 m³) glass chamber.

0.7 Ml of each oil formulation was sprayed into this glass chamber with a spray-gun at a pressure of 0.8 kg/cm², and the number of knocked-down insects was observed at 1.75 min after spraying (two replications).

The results are shown in Table 7.

TABLE

| Test compound | % Knock-down Housefly | Common Mosquito |
|---|---|---|
| (1) | 100 | 100 |
| (B) | 15 | 0 |
| (C) | 0 | 0 |
| (D) | 0 | 0 |
| (E) | 25 | 10 |
| (F) | 10 | 0 |
| No treatment | 0 | 0 |

What is claimed is:

1. A compound represented by the formula

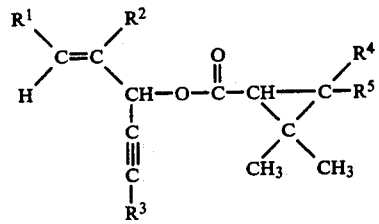

wherein R¹ represents halogenated C₁-C₄ alkyl, R² represents fluorine or methyl, R³ represents hydrogen, R⁴ represents hydrogen or methyl, and when R⁴ is hydrogen, R⁵ represents a group of the formula

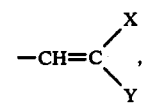

in which X and Y are the same or different and represent methyl, fluorine, chlorine, bromine or trifluoromethyl, and when R⁴ is methyl, R⁵ represents methyl.

2. A compound according to claim 1, wherein R¹ represents a 2-fluoroethyl group or a 2-chloroethyl group.

3. A compound of the formula,

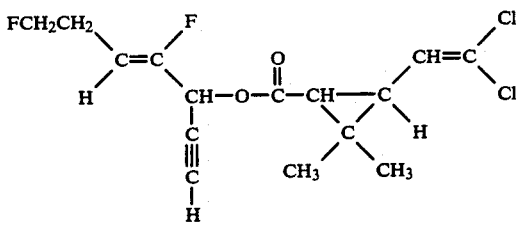

4. An insecticidal composition which comprises as an active ingredient an insecticidally effective amount of a compound represented by the formula,

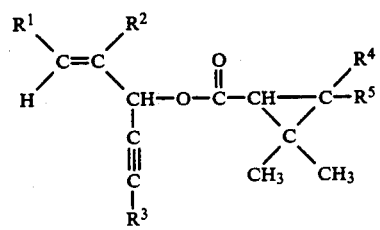

wherein R¹ represents halogenated C₁-C₄ alkyl, R² represents fluorine or methyl, R³ represents hydrogen, R⁴ represents hydrogen or methyl, and when R⁴ is hydrogen, R⁵ represents a group of the formula

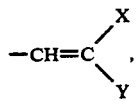

in which X and Y are the same or different and represent methyl, fluorine, chlorine, bromine or trifluoromethyl, and when R⁴ is methyl, R⁵ represents methyl and an inert carrier.

5. An insecticidal composition according to claim 4, wherein R¹ represents a 2-fluoroethyl group or a 2-chloroethyl group.

6. An method for controlling insects which comprises applying an insecticidally effective amount of a compound according to claim 2 to the insects.

* * * * *